US011065198B2

(12) United States Patent
Patankar et al.

(10) Patent No.: US 11,065,198 B2
(45) Date of Patent: Jul. 20, 2021

(54) DISPERSIBLE COMPOSITIONS

(71) Applicant: Janssen Sciences Ireland Unlimited Company, County Cork (IE)

(72) Inventors: Harshad Patankar, Raritan, NJ (US); Nicolaas Martha Felix Goyvaerts, Beerse (BE); Gopal Rajan Ranga Rajan, Beerse (BE)

(73) Assignee: Janssen Sciences Ireland Unlimited Company, Cork (IE)

( * ) Notice: Subject to any disclaimer, the term of this patent is extended or adjusted under 35 U.S.C. 154(b) by 0 days.

(21) Appl. No.: 16/344,143

(22) PCT Filed: Oct. 23, 2017

(86) PCT No.: PCT/EP2017/077030
§ 371 (c)(1),
(2) Date: Apr. 23, 2019

(87) PCT Pub. No.: WO2018/077815
PCT Pub. Date: May 3, 2018

(65) Prior Publication Data
US 2020/0069579 A1    Mar. 5, 2020

(30) Foreign Application Priority Data

Oct. 24, 2016   (IN) .............................. 201621036404

(51) Int. Cl.
| A61K 9/00 | (2006.01) |
| A61P 31/18 | (2006.01) |
| A61K 9/20 | (2006.01) |
| A61K 31/505 | (2006.01) |
| A61K 45/06 | (2006.01) |
| A61P 43/00 | (2006.01) |
| A61P 37/04 | (2006.01) |

(52) U.S. Cl.
CPC .......... *A61K 9/0056* (2013.01); *A61K 9/2013* (2013.01); *A61K 9/2018* (2013.01); *A61K 9/2027* (2013.01); *A61K 9/2054* (2013.01); *A61K 9/2077* (2013.01); *A61K 31/505* (2013.01); *A61K 45/06* (2013.01); *A61P 31/18* (2018.01); *A61P 37/04* (2018.01); *A61P 43/00* (2018.01)

(58) Field of Classification Search
None
See application file for complete search history.

(56) References Cited

FOREIGN PATENT DOCUMENTS

| EA | 021700 B1 | 8/2015 |
| WO | WO 03/016306 A1 | 2/2003 |
| WO | WO 2004/016581 A1 | 2/2004 |
| WO | WO 2005021001 A1 | 3/2005 |
| WO | WO 2006/024668 A1 | 3/2006 |
| WO | WO 2007147882 A2 | 12/2007 |
| WO | WO 2015/120014 A1 | 8/2015 |
| WO | WO 2015/136294 A1 | 9/2015 |
| WO | WO 2015/176008 A1 | 11/2015 |

OTHER PUBLICATIONS

International Search Report and Written Opinion dated Dec. 19, 2017, for International Application PCT/EP2017/077030.
Clinical Trials.gov Identifier NCT02561936, Relative Bioavailability of Three Oral Formulations Candidates of Rilpivirine for Potential Pediatric Use Compared to Oral Tablet, First Posted Sep. 28, 2015.
Official Action and Search Report in corresponding Russian Patent Application No. 2019115672 dated Jan. 21, 2021 by the Patent Office of the Russian Federation.
Chueshov, V.I. et al., "Industrial technology of drugs", Kharkov, NFAU publishing house, 2002, vol. 2, pp. 352-355.
Mashkovsky, M.D., Medicines, 14th Edition, vol. 1. Moscow, 2001, p. 11.

*Primary Examiner* — Sin J Lee

(57) ABSTRACT

The present invention is concerned with dispersible compositions comprising rilpivirine or a pharmaceutically acceptable acid addition salt thereof as an active ingredient. Such compositions are useful in the treatment of HIV infection and their dispersibility properties lend themselves to be useful in particular amongst the pediatric or geriatric population.

6 Claims, No Drawings

DISPERSIBLE COMPOSITIONS

CROSS-REFERENCE TO RELATED APPLICATIONS

This application is a 371 national phase entry of International Application No. PCT/EP2017/077030, filed on Oct. 23, 2017, which claims priority to Indian Patent Application No. 201621036404, filed Oct. 24, 2016, both of which are incorporated herein in their entirety.

The present invention concerns a pharmaceutical composition containing a certain HIV (Human Immunodeficiency Virus) agent, in particular E-4-[[4-[[4-(2-cyanoethenyl)-2,6-dimethylphenyl]amino]-2-pyrimidinyl]amino]-benzonitrile or a pharmaceutically acceptable acid addition salt thereof, in particular the hydrochloric acid salt, as active ingredient. More specifically, the invention relates to a dispersible, or disintegrating, tablet, a process for preparing it, as well as its use in the treatment of HIV infection. Such novel compositions are particularly suited to the paediatric population. It can also suit the geriatric population.

The active ingredient is E-4-[[4-[[4-(2-cyanoethenyl)-2,6-dimethylphenyl]amino]-2-pyrimidinyl]amino]-benzonitrile (rilpivirine) or a pharmaceutically acceptable acid addition salt thereof, in particular E-4-[[4-[[4-(2-cyanoethenyl)-2,6-dimethyl-phenyl]amino]-2-pyrimidinyl]amino]-benzonitrile in the form of a hydrochloric acid salt represented by the following formula:

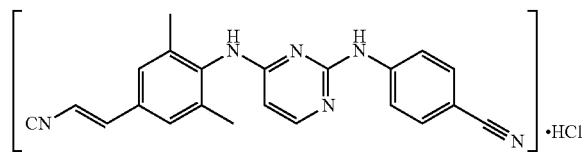

(E)

The product EDURANT™ containing this active ingredient has already received marketing approval in for instance the US and the EU.

The utility of the invention arises from the active ingredient showing activity against HIV infection, including drug and multidrug resistant HIV strains, in particular drug and multidrug resistant HIV-1 strains, more in particular the active ingredient shows activity against HIV strains, especially HIV-1 strains, that have acquired resistance to one or more art-known non-nucleoside reverse transcriptase inhibitors. Art-known non-nucleoside reverse transcriptase inhibitors are those non-nucleoside reverse transcriptase inhibitors other than the present active ingredient and in particular commercial non-nucleoside reverse transcriptase inhibitors.

The HIV replication inhibiting activity of 4-[[4-[[4-(2-cyanoethenyl)-2,6-dimethyl-phenyl]amino]-2-pyrimidinyl]amino]benzonitrile is described in WO 03/16306, which is incorporated herein by reference. WO2006/024668, which is incorporated herein by reference, discloses drug formulations comprising E-4-[[4-[[4-(2-cyanoethenyl)-2,6-dimethylphenyl]amino]-2-pyrimidinyl]amino]benzonitrile hydrochloric acid.

The present invention discloses the development of a paediatric or geriatric formulation of E-4-[[4-[[4-(2-cyanoethenyl)-2,6-dimethylphenyl]amino]-2-pyrimidinyl]amino]-benzonitrile or a pharmaceutically acceptable acid addition salt thereof, in particular the hydrochloric acid salt thereof. For the paediatric or geriatric population, it may be difficult to swallow solid compositions like tablets, and it may be desired to have a dispersible composition, in particular a dispersible tablet, and this may provide additional challenges. This is particularly so from the perspective of devising such tablets that have a suitably fast dispersion time.

There is now provided a dispersible composition (e.g. tablet) comprising E-4-[[4-[[4-(2-cyanoethenyl)-2,6-dimethylphenyl]amino]-2-pyrimidinyl]amino]-benzonitrile or a pharmaceutically acceptable acid addition salt thereof, in particular the hydrochloric acid salt thereof, as the active ingredient. This may be referred to herein as "the (dispersible) tablet of the invention".

By "dispersible", we mean a composition (e.g. tablet) that disintegrates in appropriate media, for example aqueous media (e.g. water) or other suitable media or vehicles for administration (e.g. milk, juice (e.g. orange juice) or even semi-solid like vehicles such as yogurt, apple sauce). More particularly, the composition, e.g. the tablet, disintegrates in a short period of time, in particular in a time frame of a couple of minutes, in particular 1.5 minutes or less, or 1 minute or less, or less than 1 minute, e.g. within 55 secondes or 50 seconds or 45 seconds or 40 secondes or 35 secondes or 30 secondes or less, in a small volume of medium (e.g. 50 ml or less of dispersion medium, e.g. water) such that it disperses (in particular evenly and/or rapidly) by mild swirling. Preferably, the disintegration in a suitable disintegration medium results in a drinkable liquid, for instance a drinkable suspension, or a drinkable/eatable semi-solid. In an embodiment, such a dispersion may pass through a sieve screen with a nominal mesh aperture of 710 μm.

When the dispersion occurs in a small volume of fluid, for example a 100 mg composition may be dispersed in a low quantity of water, for example as low as 1 ml to 5 ml, the resultant mixture may be described as a dispersion but also as a soft mass. For such a soft mass, this may not pass through the above-mentioned sieve screen (given the low volume of water with which it is mixed) but may nevertheless be suitable for administration, i.e. that soft mass may suitably be administered by spoon.

By "dispersed", it is meant that the composition (e.g. tablet composition) rapidly disintegrates in the dispersion medium, e.g. water, into physically smaller particles that are spread out (or dispersed) throughout the medium, e.g. water. When the composition is evenly dispersed, this results in any equal portion of the medium, e.g. water, containing approximately equal amounts of composition (e.g. tablet composition) particles (by weight), by which we mean within a deviation (% w/v) of ±25%, preferably ±15%, and especially ±10% (or less e.g. within ±5%). Hence, if a 100 mg tablet composition is dispersed in 50 ml of water, then each portion of 25 ml of water (when divided) should contain about 50 mg of tablet composition weight, but with a possible deviation of ±25% (i.e. ±12.5 mg), preferably, ±15% (i.e. ±7.5 mg) and especially ±10% (i.e. ±5 mg)—most preferably the deviation will be ±5% (i.e. ±2.5 mg). Hence, the tablet composition is physically uniform or homogenous dispersed or divided throughout the dispersion medium, e.g. water, in which it is placed (after the necessary time for dispersion; see above). It will be understood that some mild or gentle stirring or mild or gentle swirling may be applied to obtain an even dispersion of the dispersible composition, e.g. dispersible tablet, in the dispersion medium, e.g. water.

Where it is indicated that the dispersed composition (e.g. tablet composition) may pass through a 710 μm sieve, this is in order that the dispersible composition (e.g. tablet) meets certain quality thresholds/requirements, for example those in the current (or future) editions of the British Pharmacopoeia and European Pharmacopoeia. Although these properties are important for an actual dispersion in aqueous media, it will be understood that a dispersion (e.g. in water) need not be prepared, but the dispersible tablet may be administered in alternative ways. For example, the dispersible tablet may be mixed with certain foods (as such or by forming a soft mass by mixing the tablet composition with a small quantity/volume of water as described above).

For therapeutic use, salts of rilpivirine are those wherein the counterion is pharmaceutically acceptable.

The pharmaceutically acceptable addition salts as mentioned herein are meant to comprise the therapeutically active non-toxic acid addition salt forms which rilpivirine is able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxy-propanoic, 2-oxopropanoic, oxalic, malonic, succinic, maleic, fumaric, malic, tartaric, 2-hydroxy-1,2,3-propanetricarboxylic, methanesulfonic, ethanesulfonic, benzene-sulfonic, 4-methylbenzenesulfonic, cyclohexanesulfamic, 2-hydroxybenzoic, 4-amino-2-hydroxybenzoic and the like acids, whenever chemically possible. Conversely the salt form can be converted by treatment with alkali into the free base form. A preferred salt is the hydrochloric acid salt of rilpivirine.

The dispersible composition (e.g. tablet) of the invention will now be described in more details. It has properties that allow for the dispersibility (or disintegration) properties.

Hence in an aspect of the invention there is provided a dispersible composition (e.g. tablet) comprising E-4-[[4-[[4-(2-cyanoethenyl)-2,6-dimethylphenyl]amino]-2-pyrimidinyl]amino]-benzonitrile (rilpivirine) or a pharmaceutically acceptable acid addition salt thereof, in particular E-4-[[4-[[4-(2-cyanoethenyl)-2,6-dimethyl-phenyl]amino]-2-pyrimidinyl]amino]-benzonitrile in the form of a hydrochloric acid salt, as the active ingredient and wherein said active ingredient is present in the dispersible composition in the form of granules, said granules further comprising a pharmaceutically acceptable excipient (granular fraction).

Thus, the dispersible composition of the present invention comprises a granular fraction (granules) comprising E-4-[[4-[[4-(2-cyanoethenyl)-2,6-dimethylphenyl]amino]-2-pyrimidinyl]amino]-benzonitrile (rilpivirine) or a pharmaceutically acceptable acid addition salt thereof, in particular E-4-[[4-[[4-(2-cyanoethenyl)-2,6-dimethyl-phenyl]amino]-2-pyrimidinyl]amino]-benzonitrile in the form of a hydrochloric acid salt, as the active ingredient and further comprising a pharmaceutically acceptable excipient, and an extragranular fraction (the fraction of the composition next to/besides the granular fraction (the granules).

By incorporating the active ingredient in the present composition in the form of granules the manufacturability of the composition is improved. In an aspect, the compressibility and/or flowability of the final composition blend is improved in that the blend is less sticky as compared to a blend comprising the active ingredient as such, so not in the form of granules. The granules comprise active ingredient and a pharmaceutically acceptable excipient. The granules may be prepared by a dry or wet granulation process. Preferably a wet granulation process is used. Preferably a binder is used.

In an aspect of the invention the granules (the granular fraction) of the dispersible composition comprise as pharmaceutically acceptable excipient a binder.

Such a binder may be a polymer, for instance an organic polymer.

The organic polymer used in the compositions (e.g. tablets) of the invention may be any of the physiologically acceptable, preferably water soluble, synthetic, semi-synthetic or non-synthetic organic polymers.

Thus for example the polymer may be a natural polymer such as a polysaccharide or polypeptide or a derivative thereof, or a synthetic polymer such as a polyalkylene oxide (e.g. PEG), polyacrylate, polyvinylpyrrolidone, etc. Mixed polymers, e.g. block copolymers and glycopeptides may of course also be used.

The polymer conveniently has an apparent viscosity of 1 to 15,000 mPa·s when in a 2% aqueous solution at 20° C. For example, the water-soluble polymer can be selected from the group comprising alkylcelluloses such as methylcellulose,
hydroxyakylcelluloses such as hydroxymethylcellulose, hydroxyethylcellulose, hydroxypropylcellulose and hydroxybutylcellulose,
hydroxyalkyl alkylcelluloses such as hydroxyethyl methylcellulose and hydroxypropyl methylcellulose,
carboxyalkylcelluloses such as carboxymethylcellulose,
alkali metal salts of carboxyalkylcelluloses such as sodium carboxymethylcellulose,
carboxyalkylalkylcelluloses such as carboxymethylethylcellulose,
carboxyalkylcellulose esters,
starches,
pectins such as sodium carboxymethylamylopectin,
chitin derivates such as chitosan,
heparin and heparinoids,
polysaccharides such as alginic acid, alkali metal and ammonium salts thereof, carrageenans, galactomannans, tragacanth, agar-agar, gum arabic, guargum and xanthan gum,
polyacrylic acids and the salts thereof,
polymethacrylic acids and the salts thereof, methacrylate copolymers,
polyvinylalcohol,
polyvinylpyrrolidone, copolymers of polyvinylpyrrolidone with vinyl acetate,
polyalkylene oxides such as polyethylene oxide and polypropylene oxide and copolymers of ethylene oxide and propylene oxide, e.g. poloxamers and poloxamines.

Non-enumerated polymers which are pharmaceutically acceptable and have appropriate physico-chemical properties for the present composition are equally suited for preparing compositions according to the present invention.

Preferably the organic polymer is starch, polyvinylpyrrolidone or a cellulose ether, e.g. PVP K29-32, PVP K90, methyl cellulose, hydroxypropylcellulose, hydroxyethyl methylcellulose, or hydroxypropyl methylcellulose (HPMC).

Said HPMC contains sufficient hydroxypropyl and methoxy groups to render it water-soluble. HPMC having a methoxy degree of substitution from about 0.8 to about 2.5 and a hydroxypropyl molar substitution from about 0.05 to about 3.0 are generally water-soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. A preferred HPMC is hypromellose 2910 15 mPa·s or hypromellose 2910 5 mPa·s, especially hypromellose 2910 15 mPa·s. Hydroxypropyl methylcellulose is the United States Adopted Name for hypromellose (see Martindale, The Extra Pharmacopoeia, 29th edition, page 1435). In the four digit number "2910", the first two digits represent the approximate percentage of methoxyl groups and the third and fourth digits the approximate percentage composition of hydroxypropoxyl groups; 15 mPa·s or 5 mPa·s is a value indicative of the apparent viscosity of a 2% aqueous solution at 20° C.

Preferably the polymer used in the composition of the present invention is PVP K30 (povidon K30).

In an aspect of the invention the granules of the dispersible composition comprise as pharmaceutically acceptable excipient a wetting agent.

The wetting agent may increase the bioavailability of the active ingredient.

In an aspect of the invention the granules (the granular fraction) of the dispersible composition comprise as pharmaceutically acceptable excipient a binder and a wetting agent.

In an aspect of the invention the granules (the granular fraction) of the dispersible composition comprise as pharmaceutically acceptable excipient a disintegrant.

In an aspect of the invention the granules of the dispersible composition comprise as pharmaceutically acceptable excipient a wetting agent and a disintegrant.

In an aspect of the invention the granules (the granular fraction) of the dispersible composition comprise as pharmaceutically acceptable excipient a binder and a disintegrant.

In an aspect of the invention the granules (the granular fraction) of the dispersible composition comprise as pharmaceutically acceptable excipient a binder, a wetting agent and a disintegrant.

In an aspect of the invention the granules (the granular fraction) of the dispersible composition comprise as pharmaceutically acceptable excipient a diluent.

In an aspect of the invention the granules (the granular fraction) of the dispersible composition comprise as pharmaceutically acceptable excipient a binder and a diluent.

In an aspect of the invention the granules (the granular fraction) of the dispersible composition comprise as pharmaceutically acceptable excipient a wetting agent and a diluent.

In an aspect of the invention the granules (the granular fraction) of the dispersible composition comprise as pharmaceutically acceptable excipient a disintegrant and a diluent.

In an aspect of the invention the granules of the dispersible composition comprise as pharmaceutically acceptable excipient a wetting agent, a disintegrant and a diluent.

In an aspect of the invention the granules of the dispersible composition comprise as pharmaceutically acceptable excipient a wetting agent, a disintegrant and a binder.

In an aspect of the invention the granules of the dispersible composition comprise as pharmaceutically acceptable excipient a wetting agent, a diluent and a binder.

In an aspect of the invention the granules of the dispersible composition comprise as pharmaceutically acceptable excipient a diluent, a disintegrant and a binder.

In an aspect of the invention the granules of the dispersible composition comprise as pharmaceutically acceptable excipient a wetting agent, a disintegrant, a diluent and a binder.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a diluent, in particular a non-soluble diluent.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a disintegrant.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a diluent, in particular a non-soluble diluent, and a disintegrant.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a wetting agent.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a diluent, in particular a non-soluble diluent, and a wetting agent.

In an aspect of the invention, there is provided a dispersible composition (e.g. tablet) comprising E-4-[[4-[[4-(2-cyanoethenyl)-2,6-dimethylphenyl]amino]-2-pyrimidinyl]amino]-benzonitrile or a pharmaceutically acceptable acid addition salt thereof, in particular E-4-[[4-[[4-(2-cyanoethenyl)-2,6-dimethylphenyl]amino]-2-pyrimidinyl]amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a wetting agent and a disintegrant.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a diluent, in particular a non-soluble diluent, a disintegrant and a wetting agent.

The wetting agent in the extragranular fraction may ensure uniform wetting of the composition and may accelerate disintegration/dispersibility.

In an aspect of the invention, the diluent present in the extragranular fraction (so not present in the granules comprising the active ingredient) is preferable a non-soluble diluent. The presence of a non-soluble diluent (e.g. microcrystalline cellulose, such as silicified microcrystalline cellulose) may be advantageous for the dispersibility/disintegrating properties of the composition of the present invention by providing the ability to rapidly intake water of the dispersion medium, i.e. it may provide a wicking action that advantageously results in improved dispersibility/disintegrating properties. A wicking action may lead to faster dispersion and may by-pass the solubilization process (for instance, liquid may be drawn up or "wicked" into pathways through capilliary action and rupture the interparticulate bonds, causing the tablet/composition to break apart), which could be advantageous. Further, the non-soluble diluent may easily be re-suspended even after a long period of time (e.g. 6 hours)—this may have the advantage that the compositions of the invention do not require a suspending agent to re-disperse the granules/particles.

As for the wetting agent in the compositions of the invention, there may be used any of the physiologically tolerable wetting agents suitable for use in a pharmaceutical composition.

It is well-known in the art that a wetting agent is an amphiphilic compound; it contains polar, hydrophilic moieties as well as non-polar, hydrophobic moieties.

The terms "hydrophilic" or "hydrophobic" are relative terms.

The relative hydrophilicity or hydrophobicity of a wetting agent may be expressed by its hydrophilic-lipophilic balance value ("HLB value). Wetting agents with a lower HLB value are catagorized as being "hydrophobic" wetting agents whereas wetting agents with a higher HLB value are catagorized as being "hydrophilic" wetting agents. As a rule of thumb, wetting agents having a HLB value greater than about 10 are generally considered as being hydrophilic wetting agents; wetting agents having a HLB value lower than about 10 are generally considered as being hydrophobic wetting agents.

The present compositions preferably comprise a hydrophilic wetting agent. It should be appreciated that the HLB value of a wetting agent is only a rough guide to indicate the hydrophilicity/hydrophobicity of a wetting agent. The HLB value of a particular wetting agent may vary depending upon the method used to determine the HLB value; may vary depending on its commercial source; is subject to batch to batch variability. A person skilled in the art can readily identify hydrophilic wetting agents suitable for use in the pharmaceutical compositions of the present invention.

The wetting agent of the present invention can be an anionic, a cationic, a zwitterionic or a non-ionic wetting agent, the latter being preferred. The wetting agent of the present invention can also be a mixture of two or more wetting agents.

Suitable wetting agents for use in the compositions of the present invention are listed below. It should be emphasized that said list of wetting agents is only illustrative, representative and not exhaustive. Thus the invention is not limited to the wetting agents listed below. In the present compositions, also mixtures of wetting agents may be used.

Suitable wetting agents which may be used in the present invention comprise:

a) Polyethylene glycol fatty acid monoesters comprising esters of lauric acid, oleic acid, stearic acid, ricinoic acid and the like with PEG 6, 7, 8, 9, 10, 12, 15, 20, 25, 30, 32, 40, 45, 50, 55, 100, 200, 300, 400, 600 and the like, for instance PEG-6 laurate or stearate, PEG-7 oleate or laurate, PEG-8 laurate or oleate or stearate, PEG-9 oleate or stearate, PEG-10 laurate or oleate or stearate, PEG-12 laurate or oleate or stearate or ricinoleate, PEG-15 stearate or oleate, PEG-20 laurate or oleate or stearate, PEG-25 stearate, PEG-32 laurate or oleate or stearate, PEG-30 stearate, PEG-40 laurate or oleate or stearate, PEG-45 stearate, PEG-50 stearate, PEG-55 stearate, PEG-100 oleate or stearate, PEG-200 oleate, PEG-400 oleate, PEG-600 oleate; (the wetting agents belonging to this group are for instance known as Cithrol, Algon, Kessco, Lauridac, Mapeg, Cremophor, Emulgante, Nikkol, Myrj, Crodet, Albunol, Lactomul)

b) Polyethylene glycol fatty acid diesters comprising diesters of lauric acid, stearic acid, palmic acid, oleic acid and the like with PEG-8, 10, 12, 20, 32, 400 and the like, for instance PEG-8 dilaurate or distearate, PEG-10 dipalmitate, PEG-12 dilaurate or distearate or dioleate, PEG-20 dilaurate or distearate or dioleate PEG-32 dilaurate or distearate or dioleate, PEG-400 dioleate or distearate; (the wetting agents belonging to this group are for instance known as Mapeg, Polyalso, Kessco, Cithrol)

c) Polyethylene glycol fatty acid mono-and diester mixtures such as for example PEG 4-150 mono and dilaurate, PEG 4-150 mono and dioleate, PEG 4-150 mono and distearate and the like; (the wetting agents belonging to this group are for instance known as Kessco)

d) Polyethylene glycol glycerol fatty acid esters such as for instance PEG-20 glyceryl laurate or glyceryl stearate or glyceryl oleate, PEG-30 glyceryl laurate or glyceryl oleate, PEG-15 glyceryl laurate, PEG-40 glyceryl laurate and the like; (the wetting agents belonging to this group are for instance known as Tagat, Glycerox L, Capmul), e) Alcohol-oil transesterification products comprising esters of alcohols or polyalcohols such as glycerol, propylene glycol, ethylene glycol, polyethylene glycol, sorbitol, pentaerythritol and the like with natural and/or hydrogenated oils or oil-soluble vitamins such as castor oil, hydrogenated castor oil, vitamin A, vitamin D, vitamin E, vitamin K, an edible vegetable oil e.g. corn oil, olive oil, peanut oil, palm kernel oil, apricot kernel oil, almond oil and the like, such as PEG-20 castor oil or hydrogenated castor oil or corn glycerides or almond glycerides, PEG-23 castor oil, PEG-25 hydrogenated castor oil or trioleate, PEG-35 castor oil, PEG-30 castor oil or hydrogenated castor oil, PEG-38 castor oil, PEG-40 castor oil or hydrogenated castor oil or palm kernel oil, PEG-45 hydrogenated castor oil, PEG-50 castor oil or hydrogenated castor oil, PEG-56 castor oil, PEG-60 castor oil or hydrogenated castor oil or corn glycerides or almond glycerides, PEG-80 hydrogenated castor oil, PEG-100 castor oil or hydrogenated castor oil, PEG-200 castor oil, PEG-8 caprylic/capric glycerides, PEG-6 caprylic/capric glycerides, lauroyl macrogol-32 glyceride, stearoyl macrogol glyceride, tocopheryl PEG-1000 succinate (TPGS); (the wetting agents belonging to this group are for instance known as Emalex, Cremophor, Emulgante, Eumulgin, Nikkol, Thornley, Simulsol, Cerex, Crovol, Labrasol, Softigen, Gelucire, Vitamin E TPGS), f) polyglycerized fatty acids comprising polyglycerol esters of fatty acids such as for instance polyglyceryl-10 laurate or oleate or stearate, polyglyceryl-10 mono and dioleate, polyglyceryl polyricinoleate and the like; (the wetting agents belonging to this group are for instance known as Nikkol Decaglyn, Caprol or Polymuls)

g) Sterol derivatives comprising polyethylene glycol derivatives of sterol such as PEG-24 cholesterol ether, PEG-30 cholestanol, PEG-25 phyto sterol, PEG-30 soya sterol and the like; (the wetting agents belonging to this group are for instance known as Solulan™ or Nikkol BPSH)

h) Polyethylene glycol sorbitan fatty acid esters such as for example PEG-10 sorbitan laurate, PEG-20 sorbitan monolaurate or sorbitan tristearate or sorbitan monooleate or sorbitan trioleate or sorbitan monoisostearate or sorbitan monopalmiate or sorbitan monostearate, PEG-4 sorbitan monolaurate, PEG-5 sorbitan monooleate, PEG-6 sorbitan monooleate or sorbitan monolaurate or sorbitan monostearate, PEG-8 sorbitan monostearate, PEG-30 sorbitan tetraoleate, PEG-40 sorbitan oleate or sorbitan tetraoleate, PEG-60 sorbitan tetrastearate, PEG-80 sorbitan monolaurate, PEG sorbitol hexaoleate (Atlas G-1086) and the like; (the wetting agents belonging to this group are for instance known as Liposorb, Tween, Dacol MSS, Nikkol, Emalex, Atlas)

i) Polyethylene glycol alkyl ethers such as for instance PEG-10 oleyl ether or cetyl ether or stearyl ether, PEG-20 oleyl ether or cetyl ether or stearyl ether, PEG-9 lauryl ether, PEG-23 lauryl ether (laureth-23), PEG-100 stearyl ether and the like; (the wetting agents belonging to this group are for instance known as Volpo, Brij)

j) Sugar esters such as for instance sucrose distearate/monostearate, sucrose monostearate or monopalmitate or monolaurate and the like; (the wetting agents belonging to this group are for instance known as Sucro ester, Crodesta, Saccharose monolaurate)

k) Polyethylene glycol alkyl phenols such as for instance PEG-10-100 nonyl phenol (Triton X series), PEG-15-100 ocyl phenol ether (Triton N series) and the like;

l) Polyoxyethylene-polyoxypropylene block copolymers (poloxamers) such as for instance poloxamer 108, poloxamer 188, poloxamer 237, poloxamer 288 and the like; (the wetting agents belonging to this group are for instance known as Synperonic PE, Pluronic, Emkalyx, Lutrol™, Supronic, Monolan, Pluracare, Plurodac)

m) ionic wetting agents including cationic, anionic and zwitterionic surfactans such as the fatty acid salts e.g. sodium oleate, sodium lauryl sulfate, sodium lauryl sarcosinate, sodium dioctyl sulfosuccinate, sodium myristate, sodium palmitate, sodium state, sodium ricinoleate and the like; such as bile salts e.g. sodium cholate, sodium taurocholate, sodium glycocholate and the like; such as phospholipids e.g. egg/soy lecithin, hydroxylated lecithin, lysophosphatidylcholine, phosphatidylcholine, phosphatidyl ethanolamine, phosphatidyl glycerol, phosphatidyl serine and the like; such as phosphoric acid esters e.g. diethanolammonium polyoxyethylene-10 oleyl ether phosphate, esterification products of fatty alcohols or fatty alcohol ethoxylates with phosphoric acid or anhydride; such as carboxylates e.g. succinylated monoglycerides, sodium stearyl fumarate, stearoyl propylene glycol hydrogen succinate, mono/diacetylated tartaric acid esters of mono-and diglycerides, citric acid esters of mono-and diglycerides, glyceryl-lacto esters of fatty acids, lactylic esters of fatty acids, calcium/sodium stearoyl-2-lactylate, calcium/sodium stearoyl lactylate, alginate salts, propylene glycol alginate, ether carboxylates and the like; such as sulfates and sulfonates e.g. ethoxylated alkyl sulfates, alkyl benzene sulfates, alpha-olefin sulfonates, acyl isethionates, acyl taurates, alkyl glyceryl ether sulfonates, octyl sulfosuccinate disodium, disodium undecyleneamido-MEA-sulfosuccinate and the like; such as cationic wetting agents e.g. hexadecyl triammonium bromide, decyl trimethyl ammonium bromide, cetyl trimethyl ammonium bromide, dodecyl ammonium chloride, alkyl benzyldimethylammonium salts, diisobutyl phenoxyethoxydimethyl benzylammonium salts, alkylpyridinium salts, betaines (lauryl betaine), ethoxylated amines (polyoxyethylene-15 coconut amine) and the like.

When in the above list of suitable wetting agents, different possibilities are listed such as for example PEG-20 oleyl ether or cetyl ether or stearyl ether, this means that PEG-20 oleyl ether and PEG-20 cetyl ether and PEG-20 stearyl ether are intended. Thus for instance PEG-20 castor oil or hydrogenated castor oil or corn glycerides or almond glycerides has to be read as PEG-20 castor oil and PEG-20 hydrogenated castor oil and PEG-20 corn glycerides and PEG-20 almond glycerides.

Preferred wetting agents in the present compositions are sodium lauryl sulfate, sodium dioctyl sulfosuccinate, or those wetting agents belonging to the group of the polyethylene glycol sorbitan fatty acid esters, such as wetting agents known as Tween®, e.g. Tween® 20, 60, 80. Preferably the wetting agent in the granules comprising the active ingredient is Tween®, e.g. Tween® 20. Preferably the wetting agent in the extragranular fraction is sodium lauryl sulfate.

The preferred quantity of wetting agent (or surfactant) is described herein, but it is appreciated however that when used in the present compositions, it may depend e.g. on the amount of active ingredient present in the composition. A higher amount may require more wetting agent.

It is indicated herein that the compositions (e.g. tablet compositions) of the invention may contain a disintegrant. Possible disintegrants include pharmaceutically acceptable disintegrants comprising starch, ion exchange resins, e.g. Amberlite, cross-linked polyvinylpyrrolidone, modified celluloses, e.g. croscarmellose sodium (e.g. Ac-di-Sol®), sodium starch glycollate, sodium carboxymethylcellulose, sodium dodecyl sulphate, modified corn starch, microcrystalline cellulose, magnesium aluminium silicate, alginic acid, alginate, powdered cellulose, crospovidone (such as Polyplasdone XL). Other disintegrants that may be considered include L-HPC, Xanthan gum, Gellan gum, soy polysaccharides, and the like. The most preferred disintegrant for the granules comprising the active ingredient is croscarmellose sodium (e.g. Ac-di-Sol®). The most preferred disintegrant for the extragranular fraction is croscarmellose sodium (e.g. Ac-di-Sol®).

It is indicated herein that the compositions (e.g. tablet compositions) of the invention may contain a diluent. Unless that diluent is already specified, such diluent may be starch, powdered cellulose, microcrystalline cellulose (such as silicified microcrystalline cellulose), calcium phosphates (e.g. dibasic calcium phosphate, dibasic calcium phosphate dihydrate, tribasic calcium phosphate), calcium carbonate, calcium sulfate or the like (or combinations thereof, i.e. co-processed non-soluble excipients; others that may be considered include wax-like hydrogenated oils and the like). It is understood (see hereinabove) that the most preferred diluent of the extragranular fraction is a non-soluble diluent such as microcrystalline cellulose (e.g. silicified microcrystalline cellulose) because this results in compositions with intrinsic properties that are advantageous. A preferred microcrystalline cellulose is microcrystalline cellulose PH112 (Avicel® PH 112). The extragranular fraction may further comprise a second diluent, which may be more soluble. Sugars and polyols may be considered, for instance the following diluents may be considered: dextrates, dextrin, dextrose excipient, fructose, kaolin, lactitol, lactose anhydrous, lactose monohydrate, mannitol, sorbitol, sodium chloride, sucrose, compressible sugar, confectioner's sugar, a spray-dried mixture of lactose monohydrate and microcrystalline cellulose (75:25), commercially available as Microcelac®, a co-processed spray-dried mixture of microcrystalline cellulose and colloidal silicon dioxide (98:2), commercially available as Prosolv®. Preferably the extragranular fraction contains a second diluent. Preferably said second diluent is mannitol, in particular mannitol SD 200. This increases the mouthfeel of the present composition. Preferably the granules comprise a diluent. Preferably said diluent is a sugar. Preferably said sugar is lactose, i.e. lactose monohydrate.

In an aspect of the invention, there is provided a dispersible composition (e.g. tablet) comprising E-4-[[4-[[4-(2-cyanoethenyl)-2,6-dimethylphenyl]amino]-2-pyrimidinyl]-amino]-benzonitrile or a pharmaceutically acceptable acid addition salt thereof, in particular E-4-[[4-[[4-(2-cyanoethenyl)-2,6-dimethylphenyl]amino]-2-pyrimidinyl]-amino]-benzonitrile in the form of a hydrochloric acid salt, as the active ingredient and wherein said active ingredient is present in the dispersible composition in the form of granules, said granules further comprising a pharmaceutically acceptable excipient, and said composition further comprising next to the granules, in the extragranular fraction, a first diluent, in particular a non-soluble diluent, and a second diluent, in particular a sugar or a polyol. In an aspect, the first diluent is microcrystalline cellulose. In an aspect, the second diluent is a sugar. In an aspect, the first diluent is microcrystalline cellulose and the second diluent is mannitol. In an aspect the weight ratio of the first diluent and the second diluent is 1:1. In an aspect the weight ratio of microcrystalline cellulose and mannitol is 1:1. It was found that the combination of a first and a second diluent in the extragranular fraction, in particular a first non-soluble diluent, and a second, more soluble diluent, in particular microcrystalline cellulose and a sugar, in particular microcrystalline cellulose and mannitol, in particular in a 1:1 weight ratio improved the content uniformity. Content uniformity is a test prescribed in pharmacopoeiae for dosage forms, in particular tablets, wherein the dose and ratio of the active ingredients is <25 mg or <25%.

It is indicated herein that the compositions (e.g. tablet compositions) of the invention may contain a lubricant. Such a lubricant may be pharmaceutically acceptable lubricants such as magnesium stearate, calcium stearate, stearic acid, talc, polyethylene glycol, sodium lauryl sulfate, sodium stearyl fumarate, magnesium lauryl sulphate. It is most preferred that the lubricant is sodium stearyl fumarate.

It is indicated herein that the compositions (e.g. tablet compositions) of the invention may contain a glidant. Possible glidants include pharmaceutically acceptable glidants comprising talc, colloidal silicon dioxide, starch, magnesium stearate. In an aspect, the compositions of the present invention do not contain a glidant.

The compositions as described herein may further comprise one or more pharmaceutically acceptable excipients such as, for example, plasticizers, flavours, sweeteners, colorants, preservatives and the like. In an aspect of the invention, the compositions of the invention do not contain a plasticizer or another such optional excipient mentioned here.

The compositions of the present invention are characterized by a good mouthfeel and a good (rapid) disintegration.

In an aspect of the invention there is provided a dispersible composition (e.g. tablet composition) comprising by weight based on the total weight of the composition from 1 to 50%, from 1 to 30%, from 1 to 20%, from 1 to 15%, from 1 to 10%, from 1 to 5%, from 2 to 5%, from 2 to 3% of active ingredient.

In an aspect of the invention there is provided a dispersible composition (e.g. tablet composition) comprising 2.5 mg base equivalent of E-4-[[4-[[4-(2-cyanoethenyl)-2,6-dimethylphenyl]amino]-2-pyrimidinyl]amino]-benzonitrile, corresponding with 2.75 mg of E-4-[[4-[[4-(2-cyanoethenyl)-2,6-dimethylphenyl]amino]-2-pyrimidinyl]-amino]-benzonitrile HCl.

In an aspect of the invention there is provided a dispersible composition (e.g. tablet composition) comprising 5 mg base equivalent of E-4-[[4-[[4-(2-cyanoethenyl)-2,6-dimethylphenyl]amino]-2-pyrimidinyl]amino]-benzonitrile, corresponding with 5.5 mg of E-4-[[4-[[4-(2-cyanoethenyl)-2,6-dimethylphenyl]amino]-2-pyrimidinyl]amino]-benzonitrile HCl.

In an aspect of the invention there is provided a dispersible composition (e.g. tablet composition) comprising (e.g. consisting of) by weight based on the total weight of the composition:
  1 to 50% (e.g. 1 to 10% or 2 to 5%) of active ingredient
  35% to 95% (e.g. 70 to 95%) of a diluent
  0.1% to 10% (e.g. 2 to 5%) of a disintegrant
  0 to 5% (e.g. 0 to 3.5%) of a glidant
  0.01 to 5% (e.g. 0.01 to 1.5%) of a wetting agent
  0 to 10% (e.g. 0.1 to 2%) of a binder
  0 to 5% (e.g. 1 to 3%) of a lubricant.

In an aspect of the invention there is provided a dispersible composition (e.g. tablet composition) comprising by weight based on the total weight of the composition from 35% to 70% (e.g. 35 to 50%) of a non-soluble diluent, e.g. microcrystalline cellulose, such as silicified microcrystalline cellulose.

In an aspect of the invention there is provided a dispersible composition (e.g. tablet composition) comprising by weight based on the total weight of the composition from 35% to 70% (e.g. 35 to 50%) of a sugar diluent, e.g. mannitol.

In an aspect of the invention there is provided a dispersible composition (e.g. tablet composition) comprising by weight based on the total weight of the composition from 1% to 10% (e.g. 2 to 5%) of a disintegrant, e.g. croscarmellose sodium.

In another aspect, there is provided a composition (e.g. tablet composition) wherein the different parts of the composition, specifically the granular and extragranular fraction, comprise the following ingredients by weight based on the total weight of the composition:

Granular Fraction
1 to 50% (e.g. 2 to 5%) of active ingredient
1% to 8% (e.g. 5 to 8%) of a diluent
0.01 to 2.5% (e.g. 0.01 to 1.5%) of a wetting agent
0 to 10% (e.g. 0.1 to 2%) of a binder
0.1% to 5% (e.g. 0.1 to 2%) of a disintegrant
Extragranular Fraction
35% to 87% (e.g. 70 to 87%) of a diluent
1% to 5% (e.g. 2 to 5%) of a disintegrant
0.01 to 2.5% (e.g. 0.1 to 1.5%) of a wetting agent
0 to 5% (e.g. 1 to 3%) of a lubricant.

In the context of the compositions (e.g. tablet compositions) described herein, the aspects of the composition may be described as comprising a granular fraction and an extragranular fraction. Such fractions of the composition are ultimately intermingled with each other. However, it will be appreciated (for example with reference to the process for preparing such compositions) that the distinction of these fractions results in distinct properties for the resultant compositions.

The granular fraction may comprise up to 50% by weight of the total weight of the composition (e.g. tablet), and preferably comprises between 5 and 20% (e.g. between 5 and 10%) by weight of the composition (or tablet). The extragranular fraction may comprise up to 95% by weight of the total weight of the composition (e.g. tablet), and preferably comprises between 50 and 95% (e.g. between 70 and 95%) by weight of the composition (or tablet).

The compositions of the invention described herein may be a mixture of or blend of the granular and extra-granular fractions and may, after being subjected to a suitable compression technique, take on a (unit) dosage form such as a tablet.

In aspects of the invention described herein, particularly the dispersible compositions described above, the total composition weight, e.g. the total tablet weight, may be about 100 mg. The active ingredient present may range from 1 to 25 mg, such as from 1 mg to 5 mg, e.g. about 2.5 mg base equivalent (2.75 mg of the corresponding HCl salt) or e.g. about 5 mg base equivalent (5.5 mg of the corresponding HCl salt). In this manner a paediatric (or geriatric) formulation may be provided which is dispersible and which provides for dosage flexibility for the intended population, e.g. the paediatric population, e.g. children ranging between 0 and 12 years.

The invention also relates to processes for preparing the compositions of the invention (e.g. the tablet compositions) and there is therefore provided:

A process (e.g. as described herein) for the preparation of a composition (e.g. tablet) of the invention
A product (e.g. composition of the invention, e.g. a dispersible tablet as described herein) obtainable by a process of the invention (e.g. as described herein)

As indicated above, the compositions of the invention preferably comprise different fractions, a granular fraction and an extragranular fraction.

Hence, there is provided a process for the preparation of a composition of the invention, which comprises:

(a) obtaining a granular fraction using the granular fraction components mentioned herein, preferably by using a binder solution (e.g. in water) containing a binder as mentioned herein;
(b) obtaining an extragranular fraction using the extragranular fraction components mentioned herein,
and using those fractions to prepare a composition of the invention.

More specifically, the granular fraction (as defined herein) may be prepared by mixing or blending the relevant components (dry granulation, roller compaction), or, preferably, by wet granulation using a suitable binder as mentioned herein. Dry and wet granulation techniques are known to the skilled person.

The obtained granules may be dried and/or sized (or sieved).

The granules are then blended or cosifted and blended with the components of the extragranular fraction (as defined herein). Such blending also inherently involves lubrication, if the extragranular layer also includes a lubricant.

Once a composition of the invention has been prepared, for example as set out above, including the mixing of the granular and extragranular fractions, such composition may optionally, and preferably, be converted into tablet forms. In a preferred aspect of the process of the invention, the compositions so prepared are preferably compressed into tablet form, thereby allowing for the preparation of a dispersible tablet of the invention. Such a tablet may be of any suitable dose, but each unit may contain from 1 to 25 mg of active ingredient (base equivalent, not considering the salt component). The unit preferably contains from 2 to 5 mg of rilpivirine base equivalent, preferably 2.5 mg rilpivirine base equivalent, i.e. 2.75 mg of rilpivirine HCl or 5 mg rilpivirine base equivalent, i.e. 5.5 mg of rilpivirine HCl.

The tabletting process itself is otherwise standard and readily practised by forming a tablet from the desired blend or mixture of ingredients into the appropriate shape using a conventional tablet press. The hardness of the tablets is appropriate for a dispersible tablet.

Tablets of the present invention may further be film-coated to improve taste, to provide ease of swallowing and/or an elegant appearance. Many suitable polymeric film-coating materials are known in the art. A preferred film-coating material is hydroxypropyl methylcellulose HPMC, especially HPMC 2910 5 mPa·s. Other suitable film-forming polymers also may be used herein, including, hydroxypropylcellulose, and acrylate-methacrylate copolymers. Besides a film-forming polymer, the film coat may further comprise a plasticizer (e.g. propylene glycol) and optionally a pigment (e.g. titanium dioxide). The film-coating suspension also may contain talc as an anti-adhesive. In immediate release tablets according to the invention, the film coat is small and in terms of weight accounts for less than about 3% (w/w) of the total tablet weight. In an embodiment of the invention (e.g. in a preferred embodiment), the tablets of the invention are not film-coated.

As indicated above, the utility of the invention arises from the active ingredient, and salt thereof, being known to show activity against HIV.

Hence, in an aspect of the invention, there is provided compositions (e.g. tablets) according to the invention, which are suitable for the treatment of HIV infection or compositions (e.g. tablets) according to the invention for use in the treatment of HIV infection or compositions (e.g. tablets) according to the invention for the treatment of HIV infection.

Further, the present invention also relates to the use of a composition (e.g. tablet) of the invention as described hereinafter for the manufacture of a medicament for the treatment of HIV infection.

Accordingly, in another aspect, the invention provides a method of treating a patient suffering from, or at risk of, a HIV infection, in particular suffering from a HIV infection, which comprises administering to the patient a therapeutically effective amount of a dispersible composition (e.g. tablet) according to the invention.

The present compositions can be used alone or in combination with other therapeutic agents, such as anti-virals, antibiotics, immunomodulators or vaccines for the treatment of viral, e.g. HIV, infections. They may also be used alone or in combination with other prophylactic agents for the prevention of viral, e.g. HIV, infections.

Also, the combination of an antiretroviral compound and a composition of the present invention can be used as a medicine. Thus, the present invention also relates to a product containing (a) a composition of the present invention, and (b) one or more other antiretroviral compounds, as a combined preparation for simultaneous, separate or sequential use in anti-HIV treatment. The different drugs may be combined in the composition of the present invention as a single preparation together with pharmaceutically acceptable carriers. Thus, the present invention also relates to a dispersible composition as described herein and further comprising one or more other antiretroviral agents.

Said other antiretroviral compounds may be known antiretroviral compounds such as suramine, pentamidine, thymopentin, castanospermine, dextran (dextran sulfate), foscarnet-sodium (trisodium phosphono formate); nucleoside reverse transcriptase inhibitors, e.g. zidovudine (3'-azido-3'-deoxythymidine, AZT), didanosine (2',3'-dideoxyinosine; ddI), zalcitabine (dideoxycytidine, ddC) or lamivudine (2'-3'-dideoxy-3'-thiacytidine, 3TC), stavudine (2',3'-didehydro-3'-deoxythymidine, d4T), abacavir, abacavir sulfate, emtricitabine ((−) FTC), racemic FTC and the like; non-nucleoside reverse transcriptase inhibitors such as nevirapine (11-cyclopropyl-5,11-dihydro-4-methyl-6H-dipyrido-[3,2-b: 2',3'-e][1,4]diazepin-6-one), efavirenz, delavirdine, TMC-120, TMC-125 and the like; compounds of the TIBO (tetrahydro-imidazo[4,5,1-jk][1,4]-benzodiazepine-2(1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl) amino]-2,6-dichlorobenzene-acetamide and the like; inhibitors of trans-activating proteins, such as TAT-inhibitors, e.g. RO-5-3335, or REV inhibitors, and the like; protease inhibitors e.g. indinavir, ritonavir, saquinavir, lopinavir (ABT-378), nelfinavir, amprenavir, TMC-114, BMS-232632, VX-175 and the like; fusion inhibitors, e.g. T-20, T-1249 and the like; CXCR4 receptor antagonists, e.g. AMD-3100 and the like; inhibitors of the viral integrase, such as for example dolutegravir or cabotegravir; nucleotide-like reverse transcriptase inhibitors, e.g. tenofovir, tenofovir diphosphate, tenofovir disoproxil fumarate (TDF), tenofovir alafenamide (hemi)fumarate (TAF), and the like; ribonucleotide reductase inhibitors, e.g. hydroxyurea and the like; CCR5 antagonists, e.g. ancriviroc, aplaviroc hydrochloride, vicriviroc.

By administering rilpivirine with other anti-viral agents which target different events in the viral life cycle, the therapeutic effect of these compounds can be potentiated. Combination therapies as described above may exert a synergistic effect in inhibiting HIV replication because each component of the combination acts on a different site of HIV replication. The use of such combinations may reduce the dosage of a given conventional anti-retroviral agent which would be required for a desired therapeutic or prophylactic effect as compared to when that agent is administered as a monotherapy. These combinations may reduce or eliminate the side effects of conventional single anti-retroviral therapy while not interfering with the anti-viral activity of the agents. These combinations reduce potential of resistance to single agent therapies, while minimizing any associated toxicity. These combinations may also increase the efficacy of the conventional agent without increasing the associated toxicity.

The compositions of the present invention may also be administered in combination with immunomodulating agents, e.g. levamisole, bropirimine, anti-human alpha interferon antibody, interferon alpha, interleukin 2, methionine enkephalin, diethyldithiocarbamate, tumor necrosis factor, naltrexone and the like; antibiotics, e.g. pentamidine isethiorate and the like; cholinergic agents, e.g. tacrine, rivastigmine, donepezil, galantamine and the like; NMDA channel blockers, e.g. memantine to prevent or combat infection and diseases or symptoms of diseases associated with HIV infections, such as AIDS and ARC, e.g. dementia.

The term "about" as used herein in connection with a numerical value is meant to have its usual meaning in the context of the numerical value. Where necessary the word "about" may be replaced by the numerical value ±10%, or ±5%, or ±2%, or ±1%. All documents cited herein are incorporated by reference in their entirety.

For the avoidance of doubt, it is to be understood that each general or specific preference, embodiment, aspect and example as defined herein may be combined if possible with any other general or specific preference, embodiment, aspect and example as defined herein and that all such embodiments are embraced by this application.

The following examples are intended to illustrate the present invention.

EXPERIMENTAL PART

The active ingredient, rilpivirine and pharmaceutically acceptable salt thereof, may be prepared for example in accordance with the procedures described in international patent applications WO 03/16306, WO2004/016581 and WO2006/024668.

1) Preparation of a Dispersible Composition of the Present Invention

Rilpivirine HCl 2.75 mg
Lactose monohydrate
Croscarmellose sodium
Polyvinylpyrrolidone (e.g. Povidon K30)
Polysorbate 20
Purified water (removed during processing)
Total: 8.73 mg
Mannitol
Microcrystalline cellulose
Sodium lauryl sulfate
Croscarmellose sodium
Sodium stearyl fumarate
Total: 100 mg Rilpivirine HCl granules were prepared by wet granulation. The first ½ portion of lactose monohydrate 200 mesh was charged in a suitable container. Rilpivirine HCl was charged in the suitable container. Croscarmellose sodium was charged in the suitable container. The second ½ portion of lactose monohydrate 200 mesh was charged in the suitable container. The mixture was blended. The binder solution was prepared by charging purified water and povidone in a suitable vessel. Polysorbate 20 was added. The mixture was stirred. Granulation was performed in a fluid bed granulator (Glatt WSG 200). The powder blend was charged under vacuum in the granulator. The binder solution was sprayed onto the mixture. The dried material was discharged from the granulator, milled and charged in a suitable container (step 1). The granules contain 31.48% of rilpivirine HCl.

The rilpivirine containing granules were co-sifted with mannitol, microcrystalline cellulose, corscarmellose sodium and sodium lauryl sulfate using a suitable sieve and the co-sifted blend was blended using a suitable blender (step 2). Sodium stearyl fumarate was sifted, added to the blend of step 2 and the blend was lubricated using a suitable blender (step 3).

The blend of step 3 was compressed into tablets using a suitable tablet press. The resulting tablets were packed in suitable containers (e.g. high-density polyethylene (HDPE) bottles e.g. with child resistant polypropylene closure and desiccant (e.g. silica gel 2 g in HDPE pouch).

2) Identification and Quantitative Determination of Active Ingredient

To test the assay (% w/w) of the active ingredient of the composition described in 1), stored under different conditions, the following conditions were used:

HPLC Operating Conditions:
Column: Zorbax Extend C18, 100 mm length×4.6 mm i.d., 3.5 μm particle size
Column Temperature: 45° C.
Flow Rate: 1 mL/min
Injection Volume: 10 μL
Detection: UV at 280 nm
Mobile Phase: A: 10 mM ammonium acetate buffer in water
B: Acetonitrile
Elution Mode: Gradient:

| Time (minute) | A (% vol) | B (% vol) |
| --- | --- | --- |
| 0 | 95 | 5 |
| 30 | 40 | 60 |
| 31 | 40 | 60 |
| 32 | 95 | 5 |
| 37 | 95 | 5 |

Analysis Time: 37 minutes
Relative retention Time (minute): 1.0 for rilpivirine HCl.
Results for assay (% w/w) and total degradation products (% w/w) (study ID 151187: 65 tablets in 40 cc HDPE bottle with 2 g desiccant; child resistant polypropylene closure)

| Storage condition | Test interval | Assay | Total degradation product |
| --- | --- | --- | --- |
| | Initial | 101.7 | 0.3 |
| ICH light[a] unprotected[b] | 8 hours | 103.7 | 0.7 |
| ICH light[a] protected[c] | 8 hours | 100.4 | 0.3 |
| 5° C. | 1 month | 101.8 | 0.4 |
| | 3 months | 105.3 | 0.3 |
| 25° C./60% RH | 1 month | 100.5 | 0.3 |
| | 3 months | 102.4 | 0.3 |
| | 6 months | 102.2 | 0.3 |
| | 9 months | 101.3 | 0.3 |
| | 12 months | 101.3 | 0.3 |
| 30° C./75% RH | 1 month | 100.3 | 0.3 |
| | 3 months | 102.1 | 0.3 |
| | 6 months | 100.3 | 0.3 |
| | 9 months | 99.9 | 0.3 |
| | 12 months | 103.6 | 0.3 |
| 40° C./75% RH | 1 month | 99.3 | 0.3 |
| | 2 months | 102.6 | 0.3 |
| | 3 months | 102.5 | 0.3 |
| | 6 months | 98.6 | 0.3 |
| 50° C. | 1 month | 101.8 | 0.4 |

[a]integrated near UV energy not less than 200 W · h/m$^2$, overall illumination not less than 1200 klux · hr
[b]tablets were directly exposed to Light ICH in a petri dish
[c]tablets were exposed to Light ICH packed in original container Results for assay (% w/w) and total degradation products (% w/w) (study ID 151188: 65 tablets in 75 cc HDPE bottle with 2 g desiccant; child resistant polypropylene closure)

| Storage condition | Test interval | Assay | Total degradation product |
| --- | --- | --- | --- |
| | Initial | 103.4 | 0.3 |
| ICH[a] light unprotected[b] | 8 hours | 101.3 | 0.6 |
| ICH[a] light protected[c] | 8 hours | 100.3 | 0.3 |
| 5° C. | 1 month | 101.9 | 0.4 |
| | 3 months | 102.6 | 0.3 |
| 25° C./60% RH | 1 month | 102.0 | 0.4 |
| | 3 months | 102.0 | 0.3 |
| | 6 months | 102.0 | 0.3 |
| | 9 months | 100.2 | 0.3 |
| | 12 months | 102.0 | 0.3 |
| 30° C./75% RH | 1 month | 100.6 | 0.3 |
| | 3 months | 102.1 | 0.3 |
| | 6 months | 101.5 | 0.3 |
| | 9 months | 99.6 | 0.3 |
| | 12 months | 105.5 | 0.3 |
| 40° C./75% RH | 1 month | 101.2 | 0.3 |
| | 2 months | 100.9 | 0.3 |
| | 3 months | 103.5 | 0.3 |
| | 6 months | 100.4 | 0.3 |
| 50° C. | 1 month | 100.7 | 0.3 |

[a]integrated near UV energy not less than 200 W · h/m$^2$, overall illumination not less than 1200 klux · hr
[b]tablets were directly exposed to Light ICH in a petri dish
[c]tablets were exposed to Light ICH packed in original container 3) Dissolution Test To test the dissolution behavior of the composition described in 1), the following conditions were used:
Apparatus: Paddle apparatus (USP type 2);
Dissolution medium: 0.025% (w/v) polysorbate 20 (Tween® 20) in 0.01 M HCl
Volume: 900 ml
Temperature: 37° C.;
Rotation speed: 75 rpm;
Sampling time: 5, 10, 15, 20, 30, 45 and 60 minutes.
Rilpivirine HCl was measured by HPLC:
HPLC Operating Conditions:
Column: X-terra, RP18, 50 mm×4.6 mm id, 3.5 μm particle size or equivalent
Column Temperature: Elevated or Room temperature, or 35±3° C.
Flow Rate: 1.2 mL/min
Injection Volume: 50 μL
Detection: UV at 280 nm
Mobile Phase: A: 10 mM ammonium acetate pH 4.0
B: Acetonitrile Elution Mode: Isocratic (Mobile phase A: Mobile phase B) (45:55)

Analysis Time: 2.5 min[a]

[a] Retention Time (guide): Approximately 1.7 minutes for rilpivirine HCl

Results for dissolution at 45 minutes (%) (a % dissolution of at least 80% at 45 minutes was deemed acceptable for clinical testing) (study ID 151187: 65 tablets in 40 cc HDPE bottle with 2 g desiccant; child resistant polypropylene closure).

| Storage condition | Test interval | dissolution at 45 minutes (%) |
|---|---|---|
| | Initial | 97 |
| ICH[a] light unprotected[b] | 8 hours | 100 |
| ICH[a] light protected[c] | 8 hours | 101 |
| 5° C. | 1 month | 101 |
| | 3 months | 101 |
| 25° C./60% RH | 1 month | 100 |
| | 3 months | 102 |
| | 6 months | 100 |
| | 9 months | 101 |
| | 12 months | 102 |
| 30° C./75% RH | 1 month | 100 |
| | 3 months | 97 |
| | 6 months | 99 |
| | 9 months | 100 |
| | 12 months | 103 |
| 40° C./75% RH | 1 month | 99 |
| | 2 months | 99 |
| | 3 months | 102 |
| | 6 months | 98 |
| 50° C. | 1 month | 102 |

[a] integrated near UV energy not less than 200 W · h/m², overall illumination not less than 1200 klux · hr
[b] tablets were directly exposed to Light ICH in a petri dish
[c] tablets were exposed to Light ICH packed in original container Results for dissolution at 45 minutes (%) (study ID 151188: 65 tablets in 75 cc HDPE bottle with 2 g desiccant; child resistant polypropylene closure)

| Storage condition | Test interval | dissolution at 45 minutes (%) |
|---|---|---|
| | Initial | 100 |
| ICH[a] light unprotected[b] | 8 hours | 101 |
| ICH[a] light protected[c] | 8 hours | 98 |
| 5° C. | 1 month | 104 |
| | 3 months | 102 |
| 25° C./60% RH | 1 month | 99 |
| | 3 months | 100 |
| | 6 months | 100 |
| | 9 months | 98 |
| | 12 months | 99 |
| 30° C./75% RH | 1 month | 103 |
| | 3 months | 102 |
| | 6 months | 97 |
| | 9 months | 104 |
| | 12 months | 103 |
| 40° C./75% RH | 1 month | 101 |
| | 2 months | 97 |
| | 3 months | 100 |
| | 6 months | 98 |
| 50° C. | 1 month | 97 |

[a] integrated near UV energy not less than 200 W · h/m², overall illumination not less than 1200 klux · hr
[b] tablets were directly exposed to Light ICH in a petri dish
[c] tablets were exposed to Light ICH packed in original container 4) Appearance The appearance of the product was also evaluated (visual) and was considered appropriate: white to off-white round tablets.

5) Disintegration Time

The product was evaluated for disintegration in accordance with Ph. Eur.<2.9.1>.

Results for disintegration time (minutes) (study ID 151187: 65 tablets in 40 cc HDPE bottle with 2 g desiccant; child resistant polypropylene closure)

| Storage condition | Test interval | Disintegration time (minutes; 1 means higher than or equal to 30 seconds; 0 means lower than 30 seconds) |
|---|---|---|
| | Initial | 1 |
| ICH[a] light unprotected[b] | 8 hours | 1 |
| ICH[a] light protected[c] | 8 hours | 1 |
| 5° C. | 1 month | 1 |
| | 3 months | 1 |
| 25° C./60% RH | 1 month | 1 |
| | 3 months | 1 |
| | 6 months | 1 |
| | 9 months | 1 |
| | 12 months | 0 |
| 30° C./75% RH | 1 month | 1 |
| | 3 months | 1 |
| | 6 months | 1 |
| | 9 months | 1 |
| | 12 months | 0 |
| 40° C./75% RH | 1 month | 1 |
| | 2 months | 0 |
| | 3 months | 0 |
| | 6 months | 0 |
| 50° C. | 1 month | 1 |

[a] integrated near UV energy not less than 200 W · h/m², overall illumination not less than 1200 klux · hr
[b] tablets were directly exposed to Light ICH in a petri dish
[c] tablets were exposed to Light ICH packed in original container Results for disintegration time (minutes) (study ID 151188: 65 tablets in 75 cc HDPE bottle with 2 g desiccant; child resistant polypropylene closure)

| Storage condition | Test interval | Disintegration time (minutes; 1 means higher than or equal to 30 seconds; 0 means lower than 30 seconds) |
|---|---|---|
| | Initial | 1 |
| ICH[a] light unprotected[b] | 8 hours | 1 |
| ICH[a] light protected[c] | 8 hours | 1 |
| 5° C. | 1 month | 1 |
| | 3 months | 1 |
| 25° C./60% RH | 1 month | 1 |
| | 3 months | 1 |
| | 6 months | 1 |
| | 9 months | 1 |
| | 12 months | 1 |
| 30° C./75% RH | 1 month | 1 |
| | 3 months | 1 |
| | 6 months | 1 |
| | 9 months | 0 |
| | 12 months | 0 |
| 40° C./75% RH | 1 month | 1 |
| | 2 months | 1 |
| | 3 months | 1 |
| | 6 months | 0 |
| 50° C. | 1 month | 1 |

[a] integrated near UV energy not less than 200 W · h/m², overall illumination not less than 1200 klux · hr
[b] tablets were directly exposed to Light ICH in a petri dish
[c] tablets were exposed to Light ICH packed in original container 6) Fineness of Dispersion The fineness of the dispersion was tested according to Ph.eur.<2.9.1>. The acceptance criteria was passing a sieve of 710 μm.

The product stored as indicated in the above tables complied to the fineness of dispersion test.

7) Water Content

The water content was determined by Karl fisher in accordance with USP <291> method I/EP <2.5.12>.

Results for water content (% w/w) (study ID 151187: 65 tablets in 40 cc HDPE bottle with 2 g desiccant; child resistant polypropylene closure)

| Storage condition | Test interval | Water content (% w/w) |
|---|---|---|
| | Initial | 2.5 |
| ICH[a] light unprotected[b] | 8 hours | 2.2 |
| ICH[a] light protected[c] | 8 hours | 1.8 |
| 5° C. | 1 month | 2.3 |
| | 3 months | 1.9 |
| 25° C./60% RH | 1 month | 2.5 |
| | 3 months | 1.7 |
| | 6 months | 1.9 |
| | 9 months | 1.7 |
| | 12 months | 1.7 |
| 30° C./75% RH | 1 month | 2.6 |
| | 3 months | 1.9 |
| | 6 months | 1.9 |
| | 9 months | 1.9 |
| | 12 months | 1.9 |
| 40° C./75% RH | 1 month | 2.1 |
| | 2 months | 1.9 |
| | 3 months | 1.8 |
| | 6 months | 2.1 |
| 50° C. | 1 month | 2.0 |

[a]integrated near UV energy not less than 200 W · h/m², overall illumination not less than 1200 klux · hr
[b]tablets were directly exposed to Light ICH in a petri dish
[c]tablets were exposed to Light ICH packed in original container Results for water content (% w/w) (study ID 151188: 65 tablets in 75 cc HDPE bottle with 2 g desiccant; child resistant polypropylene closure)

| Storage condition | Test interval | Water content (% w/w) |
|---|---|---|
| | Initial | 2.2 |
| ICH[a] light unprotected[b] | 8 hours | 2.3 |
| ICH[a] light protected[c] | 8 hours | 1.8 |
| 5° C. | 1 month | 2.2 |
| | 3 months | 1.6 |
| 25° C./60% RH | 1 month | 2.1 |
| | 3 months | 1.7 |
| | 6 months | 1.9 |
| | 9 months | 1.9 |
| | 12 months | 1.7 |
| 30° C./75% RH | 1 month | 2.2 |
| | 3 months | 2.2 |
| | 6 months | 1.9 |
| | 9 months | 1.8 |
| | 12 months | 2.0 |
| 40° C./75% RH | 1 month | 2.2 |
| | 2 months | 1.9 |
| | 3 months | 1.9 |
| | 6 months | 2.3 |
| 50° C. | 1 month | 1.9 |

[a]integrated near UV energy not less than 200 W · h/m², overall illumination not less than 1200 klux · hr
[b]tablets were directly exposed to Light ICH in a petri dish
[c]tablets were exposed to Light ICH packed in original container 8) Content Uniformity The content uniformity was determined according to the Ph. Eur. <2.9.40> or USP <905>. The requirements for dosage uniformity were met (acceptance value of the first 10 dosage units less than or equal to L1 (L1: not more than 15.0).

The composition described in 1) was studied in a phase I, open label, randomized (according to a Williams design), four way cross over trial in healthy HIV-negative adults aged 18-55 years (Study TMC278IFD1008; NCT02561936). In the first part of the study, the dispersible tablets dispersed in water (10 tablets of 2.5 mg rilpivirine base equivalent) were taken following a standard breakfast (treatment C), and compared to the Edurant® reference tablet taken following a standard breakfast (treatment A). In the second part of the study, the dispersible tablets dispersed in water (10 tablets of 2.5 mg rilpivirine base equivalent) were taken following a standard breakfast or in fasted conditions, or dispersed in orange juice (acidic beverage) and taken after a standardized breakfast, or dispersed in water and taken with yoghurt.

Venous blood samples were collected over 168 hours after dosing for determination of rilpivirine plasma concentrations. Bioanalysis of rilpivirine in plasma was performed using a validated liquid chromatography-mass spectrometry (LC-MS/MS) method, with a lower limit of quantification of 1.0 ng/ml.

The palatability was assessed using a taste questionnaire rating bitterness, sweetness, and flavor, as well as overall acceptability using a four-point scale, and also overall taste using five point visual hedonic scale.

Administration of the dispersible tablet was generally safe and well-tolerated, both in fed and fasted conditions. The rilpivirine exposure was higher than with the 25 mg Edurant® reference tablet following a standardized breakfast (treatment C versus treatment A).

Bioavailability of the dispersible tablet taken in fasted conditions was lower than when taken with a standard breakfast. When taken with only yoghurt, the bioavailability was lower compared with a normal calorie, normal fat breakfast. Dispersion of the tablet in orange juice compared to in water increased the bioavailability. Overall the tablets showed good bioavailability, acceptable palatability, and was well tolerated.

| | Treatment A | Treatment C |
|---|---|---|
| $C_{max}$ (ng/ml) | 96.1 (±25.6) | 121 (±26.2) |
| $AUC_{0\text{-}last}$ (ng * h per ml) | 3592 (±1156) | 4310 (±1147) |
| $AUC_{0\text{-}inf}$ (ng * h per ml) | 3411 (±1449) | 4367 (±1106) |

The invention claimed is:

1. A composition having a granular fraction and an extragranular fraction, wherein the fractions comprise the following ingredients by weight based on the total weight of the composition:
   Granular Fraction
   2.75 mg of rilpivirine HCl;
   1% to 8% of a diluent;
   0.01 to 2.5% of a wetting agent;
   0 to 10% of a binder; and
   0.1% to 5% of a disintegrant; and
   Extragranular Fraction
   35% to 87% of microcrystalline cellulose;
   1% to 5% of a disintegrant;
   0.01 to 2.5% of a wetting agent; and
   0 to 5% of a lubricant.

2. The composition according to claim 1 wherein the granular fraction comprises up to 50% by weight of the total weight of the composition.

3. The composition according to claim 2 wherein the granular fraction comprises between 5 and 20% by weight of the composition.

4. The composition according to claim 1 wherein the extragranular fraction comprises up to 95% by weight of the total weight of the composition.

5. The composition according to claim 4 wherein the extragranular fraction comprises between 50 and 95% by weight of the composition.

6. The composition according to claim 1 having the following composition:

Granular Fraction
2.75 mg rilpivirine HCl; and
lactose monohydrate; and
croscarmellose sodium; and
polyvinylpyrrolidone; and
Polysorbate 20;
Total: 8.73 mg; and
Extragranular Fraction
mannitol; and
microcrystalline cellulose; and
sodium lauryl sulfate; and
croscarmellose sodium;
sodium stearyl fumarate;
Total: 100 mg.

* * * * *